United States Patent [19]

Zengel et al.

[11] 4,346,233

[45] Aug. 24, 1982

[54] PROCESS FOR THE PREPARATION OF UREAS

[75] Inventors: Hans G. Zengel, Kleinallstadt; Manfred F. Bergfeld; Rainer Zielke, both of Erlenbach, all of Fed. Rep. of Germany

[73] Assignee: Akzona Incorporated, Asheville, N.C.

[21] Appl. No.: 249,536

[22] Filed: Mar. 31, 1981

[30] Foreign Application Priority Data

Apr. 22, 1980 [DE] Fed. Rep. of Germany ....... 3015374

[51] Int. Cl.$^3$ .......................................... C07C 127/15
[52] U.S. Cl. .................................... 562/439; 548/308; 562/560; 564/45; 564/56; 564/60; 564/61; 564/118; 260/404.5
[58] Field of Search ...................... 564/45, 56, 60, 61, 564/118; 562/560, 561, 439; 548/308

[56] References Cited

U.S. PATENT DOCUMENTS

| | | | |
|---|---|---|---|
| 3,483,242 | 12/1969 | Brownstein et al. | 564/45 X |
| 4,082,749 | 4/1978 | Quadbeck-Seeger et al. | 564/61 X |
| 4,230,716 | 10/1980 | Jamieson et al. | 562/560 X |
| 4,238,404 | 12/1980 | Zengel et al. | 564/61 X |

*Primary Examiner*—Thomas A. Waltz
*Attorney, Agent, or Firm*—Francis W. Young; Daniel N. Christus

[57] ABSTRACT

This disclosure relates to a process for preparing long-chain hydrocarbon substituted ureas by reacting a long chain fatty acid N-chloramide in isopropanol and/or tertiary butanol with an aliphatic or araliphatic primary or secondary amine in the presence of an alkali or alkaline earth hydroxide at a temperature of from 20° to 100° C. The process of this disclosure is particularly useful in preparing long-chain hydrocarbon substituted ureas wherein one of the aliphatic hydrocarbon substituents contains one or more hydroxyl and/or carboxyl groups, as well as the salts of such substituted ureas.

3 Claims, No Drawings

PROCESS FOR THE PREPARATION OF UREAS

The present invention relates to a process for preparing long-chain substituted ureas utilizing long-chain fatty acid N-chloramides and aliphatic or araliphatic primary or secondary amines.

Urea derivatives with long-chain hydrocarbons are known in the art and are useful as textile auxiliaries, and as foam-stabilizing additives for anion-active detergents and cleaning agents.

The ω-ureidocarboxylic acids have acquired importance as interface-active compounds. Such ω-ureidocarboxylicacids may be prepared employing a process which comprises reacting an ω-amincarboxylic acid with urea, in the presence of a solvent and within a temperature range of from 80° to 120° C. Such procedures are described in British Pat. No. 913,713, French Pat. No. 903,848, and Italian Patent No. 226,238. However, this process requires that a large excess of urea be employed and the resulting product yield is relatively low. In addition, ω-ureidocarboxylic acids may be prepared by reacting long-chain isocyanates with amino acids as described by E. Ulsperger and G. Tuchtenhagen, in "Seifen, Oele, Fette, Wachse" 88, p. 666 (1962) and J. Prakt. Chem. 4, vol 21, p. 225 (1963). However, the isocyanates required for this process are expensive.

In addition, urea derivatives containing long-chain hydrocarbons, substituted with one or more hydroxyl groups, have acquired industrial importance. Such derivatives may be prepared employing a process which comprises reacting an isocyanate and a hydroxy-, or polyhydroxyamines in an additional reaction as described by K. Lindner in, "Tenside, Textilhilfsmittel, Waschrohstoffe", vol. 1, p. 858, Wissenschaftliche Verlagsgesellschaft m.b.H., Stuttgart 1964; E. Ulsperger, Tenside 3, p. 1 (1966). However, because the isocyanates utilized in this procedure are expensive, this process is not commercially practical.

Consequently, a need exists in the art for a process for preparing long-chain substituted urea derivatives, wherein no isocyanate starting materials are required and good yields are obtained.

The present invention relates to a process for preparing ureas of the formula

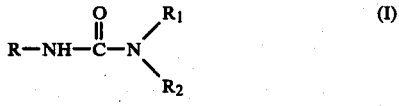

wherein R is a saturated aliphatic hydrocarbon radical having from 10 to 30 carbon atoms; $R_1$ is aliphatic radical having from 1 to 20 carbon atoms, or an araliphatic radical having from 1 to 20 carbon atoms in the aliphatic portion of the radical and having from 6 to 20 carbon atoms in the aromatic portion of the radical; and $R_2$ is hydrogen or a group represented by $R_1$; which comprises reacting a N-chloramide of a higher fatty acid of the formula

in isopropanol and/or tertiary butanol with an aliphatic or araliphatic primary or secondary amine of the formula

in the presence of an alkali hydroxide or alkaline-earth hydroxide within a temperature range of from 20° to 100° C. In addition, if necessary, water in amounts up to 50% by weight of the alcohol(s) may be added.

It is within the scope of the present invention that the class of aliphatic radicals represented by $R_1$ include both straight chain and branched chain aliphatic radicals. In addition, the class of aliphatic radicals represented by $R_1$ include aliphatic radicals substituted with one or more hydroxyl and/or carboxyl groups.

The reaction of a N-chloramide with an amine, to form a corresponding urea derivatives, is known in the art. The reaction mechanism for this process proceeds according to a so-called Hofmann reaction in the presence of amines. However, it is known that a Hofmann degradation of aliphatic carboxylic acids having eight and more carbon atoms produces primarily acyl ureas. This is further described in: C. Ferri, "Reaktionen der organischen Synthese" (Reactions of Organic Synthesis), Georg Thieme Publishing House, Stuttgart, p. 342 (1978); E. Magnien et al., J. Org. Chem. 23, 2029 (1958); and German patent 749,976, p. 1, left-hand column. Therefore, in a reactoin of a fatty acid N-chloramide, having eight and more carbon atoms, acyl ureas preponderantly should form. When higher fatty acid N-chloramides are reacted under the usual conditions of a modified Hofmann reaction, i.e. in the presence of amines and an aqueous alkali hydroxide, preponderantly acyl ureas are produced.

It has been unexpectedly found that in accordance with the process of the present invention, it is now possible to selectively convert fatty acid N-chloramides having from 10 to 30 carbon atoms into ureas while eliminating most undesirable side reactions.

The fatty acid N-chloramides employed in the process of the present invention may be obtained by chlorination of fatty acid amides, e.g. according to the process of German Pat. Nos. 749,976 and 878,491. Examples of suitable fatty acid N-chloramides include capric, lauric, myristic, palmitic, stearic, arachic, behenic, lignoceric and cerotic acid N-chloramide.

Representative of unsubstituted primary and secondary amines utilized in the process of the present invention include: methylamine, ethylamine, isopropylamine, n-propylamine, tertiary butylamine, n-butylamine, dimethylamine, diethylamine, di-isopropylamine, di-n-butylamine, di-n-amylamine, cyclohexylamine, benzylamine and α- and β-phenylethylamine.

Examples of amines having one or more carboxyl groups include glycine, alanine, valine, leucine, isoleucine, 2-aminobutyric acid, sarcosine, 3-aminobutyric acid, 4-aminobutyric acid, 4-aminohexanoic acid, 8-aminooctanoic acid, 2-aminoadipic acid, phenylglycine and phenylalanine. Examples of hydroxy-substituted amines include ethanolamine, 3-amino-1,2-propanediol, 1-amino-2-propanol, 2-amino-1-propanol, 3-amino-1-propanol, 5-amino-1-pentanol, 6-amino-1-hexanol, diethanolamine, 2-amino-1-phenylethanol, 2-amino-2- phenylethanol, N-methylglucamine, D-glucosamine and N-methylmaltoseamine.

The N-chloramides and the amine are employed in the process of the present invention in a molar ratio of from 1:1 to 1:3. It is preferred that a stoichiometric ratio of N-chloramide and amine be utilized.

The process of the present invention is carried out in the presence of an alkali hydroxide or alkaline-earth hydroxide, preferably in the presence of sodium, potassium or calcium hydroxide. The alkali hydroxide is employed in at least stoichiometric quantity with respect to the N-chloramide, i.e. one mol of alkali hydroxide, or half a mol of alkaline-earth hydroxide per mol of N-chloramide. Although a small excess of alkali may be utilized, in general, excellent yields are obtained employing stoichiometric quantities of hydroxide.

The process of the present invention proceeds within a temperature range of from 20° to 100° C., preferably from 40° C. to 60° C. It is essential that the process of the present invention proceed in the presence of isopropanol or tertiary butanol, or in a mixture of these two alcohols. If necessary, the alcohols, or the alcohol mixture, may contain up to 50% by weight of water. It must be noted that only when these above mentioned solvents or solvent mixtures are utilized, will it be possible to obtain the desired ureas in high purity. It should be noted that methanol, ethanol and propanol, are unsuitable solvents because, they will to varying extents react with the N-chloramides to form the corresponding urethanes. Water alone may also not be used as a reaction medium due to the fact that in the presence of water, acyl ureas are preponderantly formed. In addition higher alcohols may not be employed as the reaction medium, since the N-chloramides are not readily soluble in such alcohols, thereby increasing the reaction times. Furthermore when higher alcohols are employed, numerous by-products are obtained.

The quantity of solvent is not critical. In general, the process of the present invention proceeds at solvent concentrations that are as high as possible, i.e. only so much solvent is used, as is required for dissolving the N-chloramide. The reaction times are within a range from 0.5 to 3 hours and, preferably from 0.5 to 1 hour.

The process pursuant to the present invention comprises dissolving an N-chloramide in a suitable solvent, or mixture of solvents; mixing of the N-chloramide-solvent mixture with an amine and an alkali or alkaline earth hydroxide dissolved in water or other suitable solvent, and subsequently heating the resulting mixture to the required temperature. The reaction mixture is cooled and any precipitated alkali chloride, or alkaline earth chloride is removed from the reaction mixture by filtration. The filtrate is acidified with a mineral acid, and the solvent is distilled off. Generally, the desired urea precipitates in pure form from the concentrated filtrate. If desired, following the removal of the organic solvent, the urea may be extracted from the resulting aqueous residue using a suitable organic extraction solvent. The extraction solvent is then removed producing the desired urea of formula (I).

For those ureidocarboxylic acids which, by splitting off water, form a hydantoin in a warm acid medium, e.g. the ureidocarboxylic acids from sarcosine, it is preferred to acidify the reaction mixture only weakly and to remove the solvent at low temperatures, or to obtain the ureidocarboxylic acid from the reaction mixture by some other means, e.g. by extraction. It is of course also possible to recover these ureidocarboxylic acids in the form of a hydantoin and, then if desired, to split off the ureidocarboxylic acid by means of alkali.

The process of the present invention produces high yields, in a range from 60 to 90% of theoretical. Generally, the ureas of formula (I) obtained employing the process of the present invention have a high degree of purity which enables the further utilization of such ureas without further purification.

The process of the present invention is further illustrated by the following examples:

Example 1

4 g. (0.1 mol) of sodium hydroxide, dissolved in 10 ml of water, and 7.3 g. (0.1 mol) of diethylamine were simultaneously added to a solution containing 23.35 g. (0.1 mol) of lauric N-chloramide in 200 ml of tertiary butanol. The resulting mixture was heated to 40° C., and then allowed to react for 30 minutes at this temperature. Any precipitated sodium chloride was removed by filteration and the filtrate was concentrated producing a residue. The residue was taken up in 100 ml of acetone and filtered to yield 24.3 g. (90% yield) of N,N-diethyl-N'-n- undecyl urea of the formula

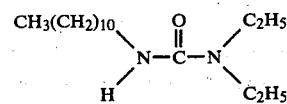

having a melting point of 33°–35° C. and the following analysis:
$C_{16}H_{34}N_2O$—molecular weight 270;
Calculated: C, 71.1%; H, 12.6%; N, 10.4%;
Found: C, 71.3%; H, 12.5%; N, 10.2%.

Example 2

To 41 g. (0.2 mol) of capric N-chloramide dissolved in 250 ml of isopropanol at 20° C. was added a mixture of 15 g. (0.2 mol) of glycine and 16 g. (0.4 mol) of sodium hydroxide dissolved in 200 ml of water. The resulting mixture was heated to 45° C. After one hour a clear, colorless solution was produced, from which part of the formed sodium chloride precipitates when it was cooled to 20° C. Afer separation of the sodium chloride, the filtrate was acidified with 10% hydrochloric acid to a pH of 3 and the precipitate was separated to yield 41.2 g. (84.4% yield) of ω-n-nonylureidoacetic acid of the formula

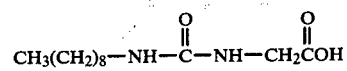

having a melting point of 144°–145° C. and the following elemental analysis:
$C_{12}H_{24}H_2O_3$—molecular weight 244;
Calculated: C, 59.0%; H, 9.8%; N, 11.5%;
Found: C, 59.2%; H, 9.8%; N, 11.6%.

Example 3

23.4 g. (0.2 mol) of valine and 16 g. (0.2 mol) of sodium hydroxide dissolved in 100 ml of water, were added to a solution containing 63.5 g (0.2 mol) of stearic N-chloramide in 600 ml of tertiary butanol. The resulting mixture was heated to 50° C., and after one hour was cooled to 20° C., and then acidified with 10% hydrochloric acid (pH 4). 500 ml of tertiary butanol was distilled from the reaction mixture to yield 6.1 g. (83% yield) of a precipitated ω-n-pentadecyl ureidoisovaleric acid of the formula

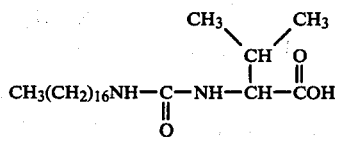

having a melting point of 216°-218° C. and the following analysis:
$C_{23}H_{46}N_2O_3$—molecular weight 398;
Calculated: C, 69.3%, H, 11.6%, N, 7.0%;
Found: C, 69.6%; H, 11.8%; N, 6.8%.

EXAMPLE 4

To 63.5 g (0.2 mol) of stearic N-chloramide dissolved in 500 ml of isopropanol at 50° C. was added a solution of 26.2 g (0.2 mol) aminohexanoic acid and 16 g (0.4 mol) sodium hydroxide in 200 ml of water. The resulting mixture was allowed to react for 1 hour at 50° C. The resulting acid was isolated as in Example 3 to yield 66 g (80% yield) of ω-heptadecyl ureidocaproic acid of the formula

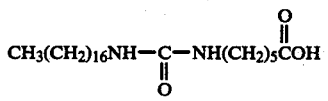

having a melting point of 108°-110° C. and the following analysis:
$C_{24}H_{48}N_2O_3$—molecular weight 412;
Calculated: C, 69.9%; H, 11.7%; N, 6.8%;
Found: C, 70.3%; H, 12.0%; N, 6.6%.

EXAMPLE 5

A solution of 26.2 g (0.2 mol) aminohexanoic acid and 16 g (0.4 mol) sodium hydroxide in 300 ml of water was added to a solution of 46.7 g (0.2 mol) lauric N-chloramide in 400 ml of isopropanol that had been heated to 40° C. The resulting mixture is heated at 50° C. for a period of 1 hour and then cooled to 20° C. The reaction mixture is acidified (pH 2) with 10% hydrochloric acid. The solvents are removed to yield 55 g (83.3% yield) of a precipitated ω-n-undecyl ureidocaproic acid of the formula

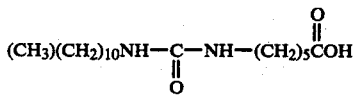

having a melting point of 103°-105° C. and the following analysis:
$C_{18}H_{36}N_2O_3$—molecular weight 328;
Calculated: C, 65.9%; H, 11.0%; N, 8.5%;
Found: C, 66.1%; H, 11.1%; N, 8.6%.

EXAMPLE 6

To a mixture containing 57.9 g (0.2 mol) of palmitic N-chloramide dissolved in 500 ml tertiary butanol at 40° C. was added 17.8 g (0.2 mol) sarcosine, 16 g (0.4 mol) sodium hydroxide and 100 ml of water. The resulting mixture was heated at 50° C. for 1 hour and then acidified with 10% hydrochloric acid (pH 3) without cooling and tertiary butanol is distilled off. During distillation, the N-methyl-N'-n-pentadecyl ureidoacetic acid precipitated was first converted into 1-methyl-3-n-pentadecyl hydantoin with splitting off of water. The initially oily hydantoin crystallized out from the aqueous distillation residue to yield 59 g (91% yield) 1-methyl-3-n-pentadecyl hydantoin of the formula

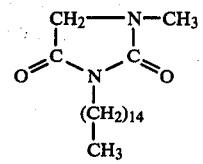

having a melting point of 58°-60° C. and the following analysis:
$C_{19}H_{36}N_2O_2$—molecular weight 324;
Calculated: C, 70.4%; H, 11.1%; N, 8.7%;
Found: C, 70.4%; H, 11.4%; N, 8.6%.

EXAMPLE 7

In accordance with the procedure described in Example 6, 41 g (0.2 mol) capric N-chloramide were reacted with sarcosine, sodium hydroxide in a mixture of tertiary butanol and water and then processed. The hydantoin remained in the aqueous solution was an oil, that was extracted with ether. The ether was removed by distillation to yield 43 g (90% yield) 1-methyl-3-n-nonyl hydantoin of the formula

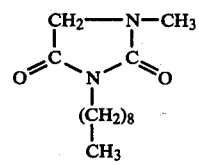

having the following analysis:
$C_{13}H_{24}N_2O_2$—molecular weight 240;
Calculated: C, 65.0%; H, 10.0%; N, 11.7%;
Found: C, 65.4%; H, 10.2%; N, 11.5%.

EXAMPLE 8

23.35 g (0.1 mol) of lauric N-chloramide, dissolved in 200 ml of isopropanol were mixed with a solution of 8.9 g (0.1 mol) sarcosine and 8 g (0.2 mol) sodium hydroxide in 40 ml of water and stirred for 1 hour at 50° C. The reaction mixture was cooled to 20° C. and any precipitated sodium chloride was removed by filtration. The filtrate was concentrated to yield a residue which was taken up in 200 ml of hot ethanol. Constituents insoluble in ethanol, such as sodium chloride were separated by filtration. The sodium salt of ureidoacetic acid crystallized out from the ethanol filtrate. The salt was filtered with suction, washed with 100 ml of acetone, and dried to yield 21.3 g (74.5% yield) of the sodium salt of N-methyl-N'-n-ureidoacetic acid of the formula

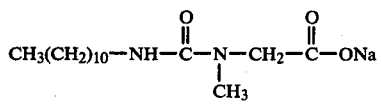

having a melting point of 151° C.

EXAMPLE 9 to 11

In accordance with the procedure described in Example 8, 0.1 mol of myristic N-chloramide, palmitic N-chloramide and stearic N-chloramide were each reacted with sarcosine/sodium hydroxide, to form the corresponding sodium salts of the N-methyl-N'-n-alkyl-ureidoacetic acids. The yields and melting points of the compounds are compiled in Table I:

TABLE I

| Example No. | Ureidoacetic acid (Sodium salt) | Melting point, °C. | Yield % |
|---|---|---|---|
| 9 | N-methyl-N'-n-tridecylureidoacetic acid | 146 | 76 |
| 10 | N-methyl-N'-n-pentadecylureidoacetic acid | 152 | 81 |
| 11 | N-methyl-N'-n-heptadecylureidoacetic acid | 143 | 78 |

EXAMPLE 12

9.34 g (40 mmol) of lauric N-chloramide were dissolved in 250 ml of isopropanol at 23° C. To the resulting clear, colorless solution was simultaneously added 1.6 g (40 mmol) of sodium hydroxide, dissolved in 10 ml of water and 4.2 g (40 mmol) diethanolamine, dissolved in 20 ml of water. The pH of the mixture initially reached 12.3 and, after 45 minutes, dropped to 9.65 (reaction temperature 50° C.). Upon termination of the reaction, the reaction product was cooled and any precipitated sodium chloride was removed by suction filtration. The filtrate was concentrated, dissolved in ethanol, and any additional sodium chloride was removed by filtration. The ethanol mixture was concentrated, to yield a viscous, slightly yellowish oil which crystallized slowly to yield 11.34 g (94% yield) of N,N-dihydroxyethyl-N'-n-undecyl urea of the formula

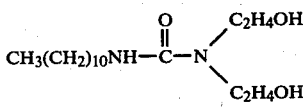

having a melting point of 42°–43° C. and the following analysis:
Calculated: C, 63.6%; H, 11.3%; N, 9.3%;
Found: C, 63.4%; H, 11.7%; N, 9.3%.

EXAMPLE 13

A mixture containing 7 g (30 mmol) of lauric N-chloramide dissolved in 200 ml of isopropanol, was reacted with a solution containing 5.85 g (30 mmol) of N-methyl-D-glucamine in 150 ml of isopropanol, 40 ml of water and 1.2 g (30 mmol) of sodium hydroxide at 50° C. for a period of 1 hour. The reaction mixture was processed in accordance with the procedures described in Example 12 to yield 7.38 g (63% yield) of N-methyl-N-(2,3,4,5,-6-pentahydroxy-n-hexyl)-N'-n-undecyl urea of the formula

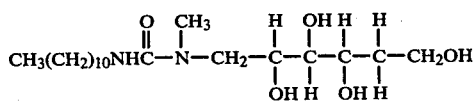

having a melting point of 109° C. and the following analysis:
$C_{19}H_{40}N_2O_6$—molecular weight 392;
Calculated: C, 58.2%; H, 10.2%; N, 7.15%;
Found: C, 57.4%; H, 10.3%; N, 7.1%.

EXAMPLE 14

In accordance with the procedure described in Example 13, 12.7 g (40 mmol) of stearic N-chloramide was reacted with stoichiometric quantities of sodium hydroxide and N-methyl-D-glucamine to yield 14 g (73.5% yield) of N-methyl-N-(2,3,4,5,6-pentahydroxy-n-hexyl)-N'-n-heptadecyl urea of the formual

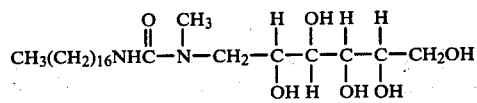

having a melting point of 94°–96° C. and the following analysis:
$C_{25}H_{52}N_2O_6$—molecular weight 476;
Calculated: C, 63%; H, 10.9%; N, 5.9%; Found: C, 63.6%; H, 10.9%; N, 5.9%.

EXAMPLE 15

In accordance with the procedure described in Example 1, 23.55 g (0.1 mol) of lauric N-chloramide were reacted and processed. However, 7.3 g (0.1 mol) of n-butylamine is utilized in lieu of diethylamine to yield 25.4 g (94% yield) N-n-butyl-N'-n-undecyl urea of the formula

with a melting point of 68° C. Upon recrystallization from ethanol, the N-n-butyl-N'-n-undecylurea had a melting point of 70° C. and the following analysis:
$C_{16}H_{34}N_2O$—molecular weight 270;
Calculated: C, 71.1%; H, 12.6%; N, 10.4%;
Found: C, 71.1%; H, 12.5%; N, 10.5%.

EXAMPLE 16

23.35 g (0.1 mol) of lauric N-chloramide, dissolved in 200 ml isopropanol, was reacted for 30 minutes with 4 g (0.1 mol) sodium hydroxide, dissolved in 10 ml of water, and 10.7 g (0.1 mol) benzylamine at a temperature of 50° C. After cooling, part of the product urea crystallized from the reaction mixture. The remaining product was precipitated with 200 ml of water. A total yield of 28.9 g (95% yield) N-benzyl-N'-n-undecyl urea of the formula

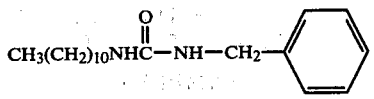

was isolated, having a melting point of 95° C. Upon recrystallization from ethanol, the N-benzyl-N'-n-undecyl urea has a melting point of 97° C. and the following analysis:
$C_{19}H_{32}N_2O$—molecular weight 304;
Calculated: C, 75.0%; H, 10.5%; N, 9.2%;
Found: C, 74.8%; H, 10.6%; N, 9.1%.

EXAMPLE 17

In accordance with the procedure described in Example 1, 40.75 g (0.1 mol) of a mixture of isomeric tolylstearic chloramides and sodium hydroxide/diethylamine in tertiary butanol were reacted to form a urea, which was processed to yield 40 g (90% yield) of N,N-diethyl-N'-tolylheptadecyl urea of the formula

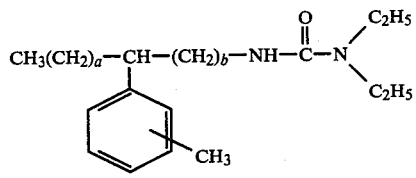

wherein $a+b=15$; as an oil having the following analysis:

$C_{29}H_{52}N_2O$—molecular weight 444;
Calculated: C, 78.4%; H, 11.7%; N, 6.3%;
Found: C, 78.0%; H, 11.9%; N, 6.1%.

EXAMPLE 18

32.4 g (0.1 mol) of 1-methyl-3-n-pentadecyl hydantoin prepared in accordance with the procedures described in Example 6 were heated overnight in 250 g of 10% soda lye under reflux conditions. After cooling 32 g (88% yield) of a sodium salt of N-methyl-N'-n-pentadecyl ureidoacetic acid of the formula

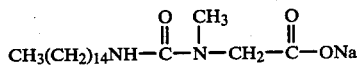

was precipitated with 1 l. of acetone and isolated.

EXAMPLE 19

A solution of 8.9 g (0.1 mol) of sarcosine and 8 g (0.2 mol) of sodium hydroxide in 40 ml of water was added to a suspension of 23.35 g (0.1 mol) of lauric N-chloramide in 200 ml of water. While the reaction mixture was heated to 50° C., acyl urea separates from the suspension in the form of flocks and was isolated by filtration to yield 17 g (86% yield) of N-n-undecyl-N'-lauroyl urea of the formula

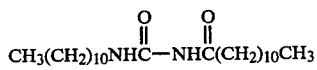

having a melting point of 104°–106° C.
105° C.; 108° C.; (literature: Jefreys, Am. 22, 33; Ehestaedt, thesis (Freiburg i.B., 1886) p. 15).

EXAMPLE 20

In accordance with the procedures described in Example 19, 31.75 g (0.1 mol) stearic N-chloramide was reacted with sarcosine/sodium hydroxide in water to yield 88% by weight of N-n-heptadecyl-N'-stearoyl urea of the formula

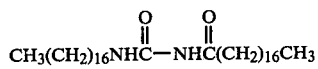

having a melting point of 110° C.
112° C. (literature: A. W. Hofmann, vol. 15, 761)

What is claimed is:

1. A process for preparing ureas wherein no isocyanate starting materials are required, said ureas being of the formula

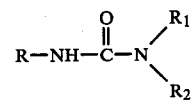

wherein R is a saturated aliphatic hydrocarbon radical having from 10 to 30 carbon atoms; $R_1$ is an aliphatic or hydroxyl- or carboxyl- substituted aliphatic radical having from 1 to 20 carbon atoms, or an araliphatic radical having from 1 to 20 carbon atoms in the aliphatic portion of the radical and having from 6 to 12 carbon atoms in the aromatic portion of the radical; and $R_2$ is hydrogen or a group represented by $R_1$; which comprises treating a N-chloramide of a higher fatty acid of the formula

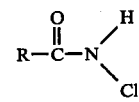

in isopropanol and/or tertiary butanol, with an aliphatic or araliphatic primary or secondary amine of the formula

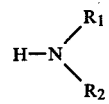

in the presence of an alkali hydroxide or alkaline-earth hydroxide within a temperature range of from 20° to 100° C.

2. A process according to claim 1, wherein the reaction is carried out within a temperature range of from 40° to 60° C.

3. A process according to claim 1 wherein in addition to isopropanol and/or tertiary butanol, water up to 50% by weight of the alcohol is employed.

* * * * *